US008597934B2

(12) United States Patent
Tobey

(10) Patent No.: US 8,597,934 B2
(45) Date of Patent: Dec. 3, 2013

(54) PROCESS FOR CONTROLLING SULFUR IN A FERMENTATION SYNGAS FEED STREAM

(75) Inventor: Richard E. Tobey, St. Charles, IL (US)

(73) Assignee: Coskata, Inc., Warrenville, IL (US)

( * ) Notice: Subject to any disclaimer, the term of this patent is extended or adjusted under 35 U.S.C. 154(b) by 420 days.

(21) Appl. No.: 12/914,632

(22) Filed: Oct. 28, 2010

(65) Prior Publication Data

US 2011/0104770 A1 May 5, 2011

Related U.S. Application Data

(60) Provisional application No. 61/256,799, filed on Oct. 30, 2009.

(51) Int. Cl.
*A61L 9/01* (2006.01)
*C12P 7/00* (2006.01)
*C12P 7/52* (2006.01)
*C12P 7/54* (2006.01)
*C12P 7/16* (2006.01)
*C12P 7/06* (2006.01)
*C12P 7/14* (2006.01)
*C12P 1/04* (2006.01)

(52) U.S. Cl.
USPC ............. 435/266; 435/41; 435/140; 435/141; 435/160; 435/161; 435/162; 435/170

(58) Field of Classification Search
None
See application file for complete search history.

(56) References Cited

U.S. PATENT DOCUMENTS

| 3,841,239 | A | 10/1974 | Nakamura et al. |
| 4,141,694 | A | 2/1979 | Camacho |
| 4,181,504 | A | 1/1980 | Camacho |
| 4,572,085 | A | 2/1986 | Hepworth |
| 4,597,777 | A | 7/1986 | Graham |
| 4,852,995 | A | 8/1989 | Cordier et al. |
| 5,478,370 | A | 12/1995 | Spangler |
| 5,504,259 | A | 4/1996 | Diebold et al. |
| 5,541,386 | A | 7/1996 | Alvi et al. |
| 5,558,698 | A | 9/1996 | Baker et al. |
| 5,593,886 | A * | 1/1997 | Gaddy ..................... 435/252.7 |
| 5,821,111 | A * | 10/1998 | Grady et al. ............... 435/252.5 |
| 6,030,430 | A | 2/2000 | Claflin et al. |
| 6,084,139 | A | 7/2000 | Van Der Giessen et al. |
| 6,340,581 | B1 * | 1/2002 | Gaddy ......................... 435/140 |
| 6,368,819 | B1 * | 4/2002 | Gaddy et al. .................... 435/42 |
| 6,755,975 | B2 | 6/2004 | Vane et al. |
| 6,899,743 | B2 | 5/2005 | Wijmans et al. |
| 6,962,683 | B2 * | 11/2005 | Gangwal et al. ........... 423/573.1 |
| 7,553,463 | B2 | 6/2009 | Zauderer |
| 7,704,723 | B2 | 4/2010 | Huhnke et al. |
| 2004/0031450 | A1 | 2/2004 | Chandran et al. |
| 2004/0120874 | A1 | 6/2004 | Zauderer |
| 2005/0218040 | A1 * | 10/2005 | Schultz et al. ................ 208/213 |
| 2007/0275447 | A1 | 11/2007 | Lewis et al. |
| 2008/0022852 | A1 * | 1/2008 | Gangwal et al. ................ 95/136 |
| 2008/0110090 | A1 | 5/2008 | Zawadzki et al. |
| 2008/0166291 | A1 | 7/2008 | McLean et al. |
| 2008/0213848 | A1 * | 9/2008 | Gaddy et al. ................... 435/161 |
| 2008/0305539 | A1 | 12/2008 | Hickey et al. |
| 2009/0029434 | A1 | 1/2009 | Tsai et al. |
| 2009/0035848 | A1 | 2/2009 | Hickey |
| 2009/0077889 | A1 | 3/2009 | Duca et al. |
| 2009/0077891 | A1 | 3/2009 | Duca et al. |
| 2009/0126273 | A1 | 5/2009 | Barnicki |
| 2009/0202717 | A1 | 8/2009 | Morra et al. |

FOREIGN PATENT DOCUMENTS

WO  2004024846 A1  3/2004

OTHER PUBLICATIONS

U.S. Appl. No. 12/891,515, filed Sep. 27, 2010.
Grethlein, A., et al., Bioprocessing of coal-derived synthesis gases by anaerobic bacteria; TibTech Dec. 1992 (vol. 10), pp. 418-423.
Misra et al., Wood Ash Composition as a Function of Furnace Temperature, Biomass and Bioenergy, vol. 4, No. 2, pp. 103-116 (1993).
Das, A. and L.G. Ljungdahl, Electron Transport System in Acetogens, Chapter 14, Biochemistry and Physiology of Anaerobic Bacteria, L.G. Ljungdahl eds,. Springer (2003).
Drake, H.L. and K. Kusel, Diverse Physiologic Potential of Acetogens, Chapter 13, Biochemistry and Physiology of Anaerobic Bacteria, L.G. Ljungdahl eds,. Springer (2003).
Andrew J. Grethlein, R. Mark Worden, Mahendra K. Jain, and Rathin Datta; Evidence for Production of n-Butanol from Carbon Monoxide by Butyribacterium methylotrophicum, Journal of Fermentation and Bioengineering, vol. 72, 1991, p. 58-60.
R. M. Worden, A. J. Grethlein, M. K. Jain, and R. Datta; Production of butanol and ethanol from synthesis gas via fermentation, Fuel, vol. 70, May 1991, p. 615-619.
Jamal Abrini, Henry Naveau, Edmond-Jacques Nyns, *Clostridium autoethanogenum*, sp. nov., an anaerobic bacterium that produces ethanol from carbon monoxide, Arch Microbiol., 1994, 345-351; Archives of Microbiology 1994, 161: 345-351.
Nitrogen Rejection, CO2 Removal, Carbon Dioxide Removal, Nitrogen Rejection Adsorption Systems, http://www.moleculargate.com/, Guild Associates, Dublin, OH, Oct. 25, 2010.

* cited by examiner

*Primary Examiner* — Chris R Tate
*Assistant Examiner* — Douglas F White

(57) ABSTRACT

Ethanol and other liquid products are produced from biomass using gasification of the biomass to produce a syngas containing CO2, CO, H2 and sulfur or sulfur compounds that passes the syngas to a fermentation step for the conversion of the CO and CO2 and H2 to ethanol. Sulfur and sulfur compounds in the syngas are used to satisfy sulfur demanded by bacteria in the fermentation step. A sulfur control additive is added to the gasification to control syngas sulfur and sulfur compounds at a desired concentration to meet bacteria sulfur demand.

25 Claims, 3 Drawing Sheets

PROCESS FOR CONTROLLING SULFUR IN A FERMENTATION SYNGAS FEED STREAM

CROSS-REFERENCE TO RELATED APPLICATIONS

This application claims the benefit of U.S. Provisional Patent Application Number 61/256,799 filed Oct. 30, 2009, which is incorporated in its entirety herein by this reference.

FIELD OF THE INVENTION

This invention relates to the production of synthesis gas and the biological conversion of CO and mixtures of CO2 and H2 to liquid products.

DETAILED DESCRIPTION

Background

Biofuels production for use as liquid motor fuels or for blending with conventional gasoline or diesel motor fuels is increasing worldwide. Such biofuels include, for example, ethanol, propanol, and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses, and other agricultural residues may become viable feedstocks for biofuel production. However, the heterogeneous nature of lignocellulosic materials, which enables them to provide the mechanical support structure of the plants and trees, makes them inherently recalcitrant to bioconversion. Also, these materials predominantly contain three separate classes of components as building blocks: cellulose (C6 sugar polymers), hemicellulose (various C5 and C6 sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the C5 sugars to ethanol, and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi-conversion processes.

An alternative technology path is to convert lignocellulosic biomass to syngas (also known as synthesis gas, primarily a mix of CO, H2, and CO2 with other components such as H2S, low molecular weight hydrocarbons, primarily methane, and other less significant or trace gases) and then to ferment this gas with anaerobic microorganisms to produce biofuels such as ethanol, propanol, and n-butanol, or chemicals such as acetic acid, butyric acid, and the like. This syngas path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, propanol, n-butanol, or other chemicals with high (e.g., greater than 90% of theoretical) efficiency.

In addition to biomass, syngas can be produced from many other carbonaceous feedstocks such as natural gas, reformed gas, peat, petroleum coke, coal, solid waste, and land fill gas, making this a more universal technology path. In general, biomass and the other carbonaceous feedstocks are made up primarily of carbon, hydrogen, and some oxygen, but can also contain calcium, potassium, magnesium, sulfur, phosphorus, manganese, zinc, iron, aluminum, sodium, silicon, boron, copper, and so forth. The latter elements and related compound contribute to syngas compounds other than CO, H2, and CO2, such as H2S, and/or a gasifier residue, such as ash or slag.

The syngas technology path requires that the syngas components CO and H2 be efficiently and economically dissolved in the aqueous medium and transferred to anaerobic microorganisms that convert them to the desired products. Also, very large quantities of these gases are required. For example, the theoretical overall equation for ethanol production from syngas is:

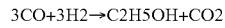

$$3CO + 3H2 \rightarrow C2H5OH + CO2$$

The relatively insoluble gases such as CO or H2 have to transfer to an aqueous medium for each mole of ethanol produced. Other liquid products such as acetic acid, propanol, and n-butanol have similar large stoichiometric requirements for the gases.

The anaerobic microorganisms that bring about these bioconversions generate very little metabolic energy from these bioconversions, and do require some sulfur to maintain biological activity. Consequently, the relatively slow growth of the microorganisms, which often continue the conversions during the non-growth phase of their life cycle to gain metabolic energy for their maintenance, can depend on available sulfur.

As the theoretical equation shows, the components of the syngas primary inputs into the production of the desired products comprise CO and H2 and CO2, and the essential feed components for supply to the microorganisms comprise CO and H2. The syngas bioconversion processes can specifically use the CO and H2/CO2 to high conversion to make products such as ethanol, acetic acid, propanol, butanol, etc. Such bioconversion processes ordinarily operate at moderate pressures and low temperatures.

Gasification processes are well known in the production of syngas. Heating of gasification process feeds and other reactants to reaction temperature can induce desired chemical reactions. Gasification processes that use oxygen and/or electricity to generate plasma or molten residue achieve very high temperatures and good residence times for syngas production. Such processes primarily produce CO and H2/CO2 that are usable by the bioconversion processes. In addition, the syngas includes H2S and other sulfur compounds of 150 ppm or higher, some of which is also usable by the bioconversion processes. Gasifiers include updraft gasifiers and downdraft gasifiers and have the principle advantage of very simple design and direct heat transfer from the thermal gases to the biomass. A disadvantage of these types of gasification systems is the energy input for generating heat, particularly electrical energy for generating plasma in the case of plasma gasification and the supply of oxygen where the direct gasification is oxygen blown.

H2S and sulfur compounds play a complex role in bioreactor and its effect on the microorganisms contained therein. Syngas sulfur in excess of microorganism needs is detrimental to microorganism activity for converting syngas to liquid products. However, sustaining the microorganisms requires a certain presence of sulfur.

Separation of unnecessary H2S or other sulfur compounds from the syngas before entering the bioreactor adds considerable process expense. First, there is the cost of the extra separation equipment that must process all or a large part of the syngas, of which the sulfur compounds may comprise a minor portion, typically on the order of 600-800 ppm, and often much less for a syngas produced by a plasma type gasifier. Such sulfur containing gases that include significant amount of H2S are known as sour gases. Amine sweetening, one of a number of processes for treating sour gases, scrubs H2S from the syngas with aqueous solutions of various alkanolamines. The H2S recovered from the sour syngas is typically converted to elemental sulfur in a Claus or other process. Sour gas treating and sulfur recovery have significant cost and operating disadvantages that can impact commercial viability. Therefore the cost associated with the equipment and its operation to remove the sulfur from the raw syngas stream makes such recovery impractical.

Depending on the gasifier feed sulfur the H2S content of such gasifier syngas can vary and be in the range of 150 to 800 ppm for woody biomass, and considerably higher for other high sulfur content carbonaceous materials. Considering that biomass sulfur can be converted into sulfur compounds in the gasification process, the syngas sulfur can be used to meet microorganism requirements for sulfur. Thus, for the biomass feed sulfur to be efficiently utilized to make ethanol or other products, a portion of this biomass sulfur needs to be converted to sulfur compounds and fed to the bioconversion process with the syngas to provide an amount of sulfur that the microorganism can effectively use.

SUMMARY OF THE INVENTION

It has been found that bioconversion processes can be used to simply and efficiently separate sulfur from the syngas of a gasifier. In this process, sulfur containing syngas passes to the bioconversion process wherein it consumes the CO, H2/CO2, and sulfur compounds to a very high extent and the exhaust gas will be primarily CO2. Use of the bioconversion process to consume the CO and H2/CO2 also has the advantage of removing syngas sulfur without the addition of expensive sulfur removal steps. Thus, this invention enables the utilization of sulfur containing syngas in a bioconversion processes to make ethanol or other fuels and chemicals. The sulfur in the syngas has beneficial effects on the operation of the bioreactors, particularly the supply of the metabolic sulfur demand of the microorganisms, which is needed to maintain microorganism activity to efficiently convert the CO and H2/CO2 to the ethanol and other products. The additional mass volume of gas passing through the system by virtue of the sulfur compound presence adds little to the cost of the bioreactors. The feed gas may pass through the bioreactor in single or multiple passes to consume CO and H2. The exhaust gas becomes predominantly CO2.

In one aspect, this invention is a process for the production of liquid products from a carbonaceous feed by gasification of the feed to syngas comprising CO2, CO, H2 and gaseous sulfur compounds, such as H2S followed by bio-conversion of syngas components. The process includes the steps of providing a carbonaceous feed to a gasifier and heating the carbonaceous feed to produce a syngas comprising CO2, CO, and H2; and converting a controlled amount of carbonaceous feed sulfur into syngas sulfur compounds. The carbonaceous feed is preferably biomass. A portion of the biomass or other carbonaceous material, such as coke, can be used as fuel to heat the remainder of the biomass to produce syngas. The process passes a feed gas comprising syngas from the gasifier to a bioreactor to convert CO and CO2 and H2 to liquid products by contact with microorganisms therein, while also utilizing sulfur compounds in the syngas to satisfy the metabolic sulfur demand of the microorganisms. A bioreactor effluent stream containing the liquid products from the bioreactor is removed from the bioreactor and liquid products are recovered from the effluent stream. Tail gas streams are also recovered from the bioreactor that comprises mainly CO2 and low molecular weight hydrocarbons such as methane, and other less significant or trace gases. The liquid products recovered from the bioreactor process will typically comprise at least one of ethanol, acetic acid, propanol, butanol, or butyric acid. The preferred liquid product for production from the process is ethanol. Waste biomass from the bioreactor process made up of spent microorganisms can be recycled back to the gasifier feed.

The process can convert almost any solid carbonaceous source of material into usable liquid products. All materials that can produce a sulfur containing syngas from gasification processes are suitable for this invention. The invention may be useful for conversion of any carbonaceous feed into liquid products via fermentation. Suitable carbon sources include coke, coal, and peat. Preferred carbon sources comprise biomass and include wood, miscanthus, switchgrass, sugar cane bagasse, and corn stover. Other carbon sources can comprise construction and demolition debris along with urban waste or biomass waste from bioconversion processes.

The process will have significant advantage where the gasification process produces enough sulfur compounds to meet microorganism sulfur demand. Typically the process finds good application where the bioreactor feed syngas contains about 150 ppm H2S on an anhydrous basis. Generally, the uncontrolled gasifier syngas on an anhydrous basis comprises 20 to 45 mole % H2, 15 to 50 mole % CO, 10 to 20 mole % CO2, and 150 to 800 ppm H2S.

The process also offers the flexibility of using a portion of carbonaceous feed sulfur to supply the sulfur demand of microorganisms in the bioreactor. When the amount of sulfur being supplied in the syngas to the bioreactor exceeds the sulfur required by the microorganisms, a sulfur control additive can be added the gasification process to control the concentration of sulfur in the syngas. The sulfur control additives can be the oxides, salts, or elemental form of transition metals.

In a more specific form, the invention is a process for the production of ethanol or other liquid products from a biomass feedstock by gasification to syngas comprising CO2, CO, H2, and H2S, followed by bio-conversion of syngas components. The process comprises providing a sulfur containing biomass feedstock to a gasifier and gasifying the biomass feedstock by contact with a heating medium at a temperature of greater than 800° C., preferably 1000 to 1200° C., and a pressure range from a slight vacuum (13 psia) to about 11 bars absolute to produce a syngas stream including CO2, CO, H2 and 150 to 800 ppm H2S on an anhydrous basis. The syngas also includes low molecular weight hydrocarbons such as methane, and other less significant or trace gases. A sulfur control additive, such as iron oxide, can be charged to the gasification process heated zone where sulfur in the biomass feed reacts with a sulfur control additive to produce oxysulfides and sulfides, which are removed from the gasification process with the gasifier residue. Addition rates of a sulfur control additive, such as a metal oxide, can be adjusted to control the H2S concentration of the syngas feed to the bioreactor. The process passes a feed gas comprising syngas from the gasifier to a bioreactor to convert CO and CO2 and H2 to ethanol by contact with microorganisms therein. A bioreactor effluent stream containing ethanol or other liquid products from the bioreactor is withdrawn and the ethanol or other liquid products are separated in a recovery section to produce a liquid product, such as an ethanol product. Tail gas stream from the bioreactor is predominately CO2, but can also include low molecular weight hydrocarbons such as methane, and other less significant or trace gases, plus any sulfur compounds not utilized in the bioreactor. Depending on specific needs, tail gas treatment can include hydrocarbon (for example, methane) recovery, conventional thermal oxidation treatment, SOX treatment, and CO2 recovery.

DETAILED DESCRIPTION OF THE INVENTION

Practical production of ethanol or other liquid product from biomass requires the effective coupling of four different process steps. First, a gasification step that converts biomass into syngas, defined to mean at least one of CO or a mixture of CO2 and H2. A gas conditioning step typically conditions the raw syngas by cooling the syngas to prepare it for consumption by the microorganisms in a fermentation step. In the fermentation step, a bioreactor receives the syngas feed and delivers it to the microorganisms that expel a liquid product such as ethanol into fermentation liquid. Finally, a separation step must recover ethanol from the broth in an energy efficient manner coupled with the rejection of tail gases that contain CO2. The practice of this invention includes the additional step of sulfur control and optionally adding a sulfur control additive to the gasification step to control the sulfur in the syngas feed to the fermentation zone.

Since sulfur is not utilized nor desirable in even a small amount by many syngas conversion processes for the production of liquid fuels, the common approach has been to remove syngas sulfur compounds directly before the conversion process. This approach requires that syngas sulfur compounds be completely removed, and thus overlooks the sulfur needed by microorganisms in bioconversion to maintain biological activity to convert the syngas to liquid products. This invention recognizes that controlled sulfur content syngas poses no significant drawbacks in the operation of the bioconversion zone, while offering significant advantages in enabling the utilization of syngas processes that produce sulfur containing syngas.

Figure 1:
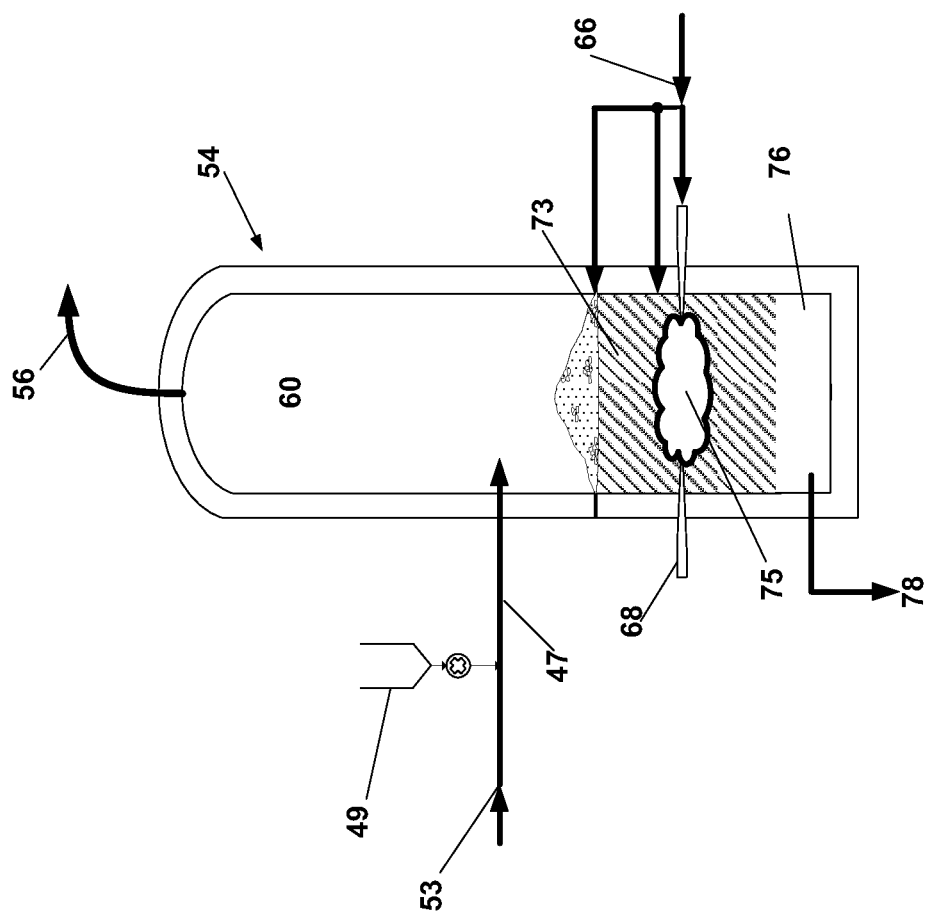
FIG. 1 is a schematic drawing of a process arrangement showing a gasification process for the generation of a sulfur containing syngas for use in the biological conversion to liquid products in accordance with this invention.

FIG. 1 gives a general overview of a gasification process 54 for the generation of a sulfur containing syngas for use in the biological conversion to liquid products and shows the major components of the process operation in simplified form. Woody biomass is optionally mixed with coke or coal, and the mixture is conveyed via transfer lines 53 and 47 to the gasifier or gasification reaction chamber 60. The woody biomass has about 20% moisture content prior to entering the gasification process section 54. If necessary, the woody biomass may pass through an optional drier to adjust its moisture content.

The gasification section converts the woody biomass into the primary syngas stream carried by a line 56. A solids transport system can be provided which conveys the woody biomass at a continuous controlled rate to the gasification reaction chamber 60 where hot gasification reaction products intensely contacts the biomass to produce a syngas and a heterogeneous residue 73. The syngas flows out of the top of chamber 60. The residue 73 flows downward and into a heated zone 75 where the residue is contacted with a plasma gas generated from a plasma torch 68. A heat transfer material (for example, coke or coal) that enters the gasification reaction chamber 60 with the biomass feed flows downward into the bottom section of the chamber where it is used to distribute and transfer the energy from the high energy section inside the reactor (plasma torches in plasma driven system). This material is consumed to produce process energy if it is a non-inert material. Alternatively, steam, air, and oxygen can be added at various points via at least one injection line 66 to the residue 73. Steam or air charged to the gasifier can be used to control gasification chamber temperature and syngas composition through known reactions with carbon and CO present in the gasification chamber. The high density non-carbon material, which is residue derived from the woody biomass feed into the reactor, moves downward through the reaction section into the bottom of the gasification reaction chamber 60. Sufficient heating of the residue forms a molten slag 76 that is collected in the bottom of the gasification reaction chamber 60. Molten slag 76 can be removed from the gasification reaction chamber 60 and cooled to form a solid residue or slag product withdrawn by line 78.

A sulfur control additive from a hopper 49 can be combined with the woody biomass feed and added via transfer line 47 to the gasification reaction chamber 60. The sulfur control additive becomes part of the residue 73 and flows downward in the gasification reaction chamber 60. Proximate to the heated zone 75, the sulfur control additive reaches the desired temperature and reacts to remove sulfur compounds that may otherwise end up in the syngas. The reacted sulfur control additive, which contains sulfur that has reacted with the additive, flows to the bottom of the gasification reaction chamber 60 with the residue. Optionally, a residue melting point modifier can also be added via transfer line 47. The residue melting point modifier can be used to adjust the temperature at which the residue becomes molten, and to aid in the vitrification of the residue or slag.

Gasification systems for the production of syngas are well known (See, U.S. Pat. No. 4,141,694; U.S. Pat. No. 4,181,504; WO 2004/024846; and US 2009/0077889 A1). This invention provides an advantage when using gasification systems to generate syngas that also have a heated zone that is operable to control the concentration of sulfur compounds in the syngas. For purposes of this invention, a significant amount of H2S would equal 150 ppm or more of the syngas on an anhydrous basis. The process also applies to higher concentration of H2S in the syngas stream that can equal 600 or 800 ppm or more on an anhydrous basis.

One common form of biomass gasification processes uses a plasma torch. Such systems generally consist of a biomass feed system, a reaction vessel or chamber (gasification or partial oxidation and/or combustion reactor), and optional gas/solids separation equipment, such as cyclones. Biomass is fed into a gasification reaction chamber, using a solid feed handling system, at a continuous flow and a prescribed rate. In the gasification reaction chamber, a heat carrying/transfer material rapidly heats the biomass in substoichiometric oxygen or an oxygen-free environment converting it into syngas and residue at approximately 900° C. The residue flows downward as it is consumed in a high temperature heated zone of the gasifier. While the gasification step can operate under a wide range of pressures from a slight vacuum (13 psia) to 11 bars absolute or more, it is preferable to operate the gasification step at a pressure compatible with the bioreactor system. Therefore, pressures will usually be at least 4 bars absolute, but can go 11 bars absolute or higher. Usually the gasification step gasifies the biomass under partial oxidation conditions. Under such conditions, the oxygen or air is substantially consumed during the gasification process, leaving the syngas produced with an oxygen concentration of less than 1 mol % in the gasification reaction chamber. Any particulate residue transported overhead with the syngas enters a gas/solid separating system. The syngas exiting the separation system is the product syngas going to heat recovery and syngas cleanup as required.

Reactants such as steam, air, and oxygen are introduced to react with any coke, coal, or biomass byproducts present, and to produce syngas and a residue typically in the form of a molten slag. In the heated zone of the gasification reaction chamber, carbon-free residue is consumed by operation of plasma torches to form a liquid residue. As known in the art, air and oxygen can be used to partially combust carbon to mainly form carbon monoxide. Steam, on the other hand, is used to react with any available carbon from biomass or other carbonaceous feeds and carbon monoxide in the syngas to increase the production of hydrogen. Thus, steam can be used to adjust syngas composition. The syngas leaves the gasification reaction chamber at about 900° C. Essentially, all of the biomass carbon is decomposed into volatile product in the gasification reaction chamber leaving a carbon-free residue. The syngas and any particulates are transported overhead where the particulates are separated. The syngas can be used for additional heat recovery. Depending on gasifier and operating conditions, the residue can be produced in the form of an agglomerated ash or molten slag that exits from the bottom of the gasification chamber.

Gasification technologies can have a high temperature region where the biomass is consumed and/or gasified at temperatures of at least 500° C., and typically at least 800° C. Examples of various types of gasification technologies, such as the Lurgi gasifier, the Atgas process, the Arc-Coal process, and others, are discussed by Salvador L. Camacho in U.S. Pat. No. 4,141,694. In the heated zone of most gasification processes, the gasifier residue is formed. The residue is generally a heterogeneous mixture of biomass ash and non-consumable tramp feed components, such as various types of debris associated with biomass collection and storage. The energy needed to create the gasifier heated zone can be supplied through electric or chemical sources. Electric power is typically supplied through a plasma arc or a plasma torch. Chemical energy for the heated zone can come from the partial oxidation and/or combustion of either supplemental coke or coal or the biomass. Some gasification processes utilize a combination of electric and chemical sources to supply the energy needed in the heated zone, which can reach temperatures as high as 4,000° C., but are more typically in the range of 2500 to 3100° C. Typical plasma systems operate about 2800° C. In the heated zone of such gasification process, a significant amount of the biomass ash sulfur can be released and/or converted into sulfur compounds that end up in syngas. Depending on the available sulfur and other biomass feed constituent, the concentration of sulfur and sulfur compounds in the syngas can be greater than the amount needed in the downstream bioreactor. However, a sulfur control additive added to the gasification reactor chamber can control syngas sulfur compound concentration at a desired level as required by the bioreactor.

Biomass contains a variety of elements such as calcium, potassium, magnesium, sulfur, phosphorus, manganese, zinc, iron, aluminum, sodium, silicon, boron, copper, and so forth. Some of the minerals are believed to be taken up by plants from the soil as sulfates and phosphates. The plant then transports and stores the minerals in both organic and inorganic forms. Much of the inorganic forms end up in the biomass ash. As shown in Table 1, biomass ash composition can vary significantly in terms of sulfur and other transition metals.

TABLE 1

Elemental Analysis of Biomass Ash at 600 deg C.

| Component, wt % | Pine | Red Oak | White Oak Bark |
|---|---|---|---|
| Magnesium | 7.03 | 5.2 | 0.34 |
| Sulfur | 1.07 | 1.80 | 0.40 |
| Manganese | 4.04 | 1.49 | 0.16 |
| Iron | 0.58 | — | 0.01 |

Misra et al., Wood Ash Composition as a Function of Furnace Temperature, Biomass and Bioenergy, Vol. 4, No. 2, pp. 103-116 (1993)

Any portion of the syngas that is fed to the bioreactor can contain sulfur compounds. In a preferred embodiment, the concentration of sulfur compounds in the syngas is controlled to meet the sulfur demanded by the downstream bioreactor. Upon entering the gasification reactor chamber, the biomass will readily release the organic sulfur. However, inorganic sulfur is typically more tightly held in the form of sulfates of calcium and potassium in the non-volatile ash portion of the biomass residue. As the heap of biomass residue in the lower portion of the gasification reaction chamber is consumed, the biomass ash eventually comes in contact with the gasification process heated zone, where residual biomass feed sulfur is reduced and released in the form of H2S or other gaseous sulfur compounds, which become part of the syngas that is carried overhead. The syngas now comprises CO, CO2, H2, H2S, and low molecular weight hydrocarbons, such as methane, and other less significant or trace gaseous contaminates that requires clean-up prior to entering a bioreactor zone. The gas clean-up can include removal of contaminates by products and particulates. Typical removal steps will extract any deleterious materials that would have any adverse effects with respect to the biological conversion zone. The syngas cleanup typically involves removal of hydrocarbon byproducts and minor contaminates such as particulates, HCl, etc., which can be removed if required.

Sulfur control additives that control the concentration of sulfur compounds in the syngas can be added to the gasification system. The additives can be added to the biomass feed or injected directly into the gasification reaction chamber at a desired location to maximize effectiveness of the additive. This invention considers sulfur control additives that are elemental transition metals and/or their oxides and/or salts. Such transition metals include, but are not limited to, lead, iron, zinc, manganese, tin, antimony, silver, copper, cobalt, chromium, and nickel. The choice of transition metal is made to optimize sulfur control and preferred removal technique of the resultant metal sulfide. In a preferred embodiment, metal oxides, such as iron oxide, are selected as the sulfur control additive. Upon entering the heated zone of the gasification reaction chamber, the metal oxide is either partially or completely reduced to the elemental metal and reacts with available sulfur liberated from the biomass to produce a metal oxysulfide and/or metal sulfide. The metal oxysulfide and/or metal sulfide combine with other biomass ash or feed components to form a heterogeneous residual product. Depending on the temperature of the heated zone, the residual product can be in the form of clinkers, an agglomerated slag or ash, or a molten slag. In a preferred embodiment, a plasma torch is used to heat the gasification reaction chamber heated zone to a temperature high enough to produce a molten slag.

Other additives, such as a residue melting point modifier or flux, can also be added to the gasification reactor chamber either in combination with the sulfur control additive or separately as required to maximize the effectiveness of the flux. The residue produced during the gasification of biomass is a heterogeneous mixture of material that generally includes components of the biomass ash, as well as tramp contaminants from biomass collection and storage, which can include clays and other earthen material. Silicas in the biomass ash and tramp materials can have very high melting points. Vitrification of the gasifier residue can include the addition of flux to lower slag melting points so as to produce a free flowing molten slag. Fluxes can include, but are not limited to, potassium, lithium, calcium, magnesium, barium, strontium, and related carbonates and silicates. Further, some minerals, such as dolomite or calcium magnesium carbonate, can act as both a flux and a sulfur control additive.

When using wood chips and most other biomass sources, the removal of the other minor source contaminates in the raw syngas from the gasifier is not expected to be complicated and can be achieved with standard scrubbing systems. Heat recovery systems are usually installed between the gasification reaction chamber and the remaining gas clean-up systems where steam or hot water can be generated to benefit on-site energy requirements.

Figure 2:
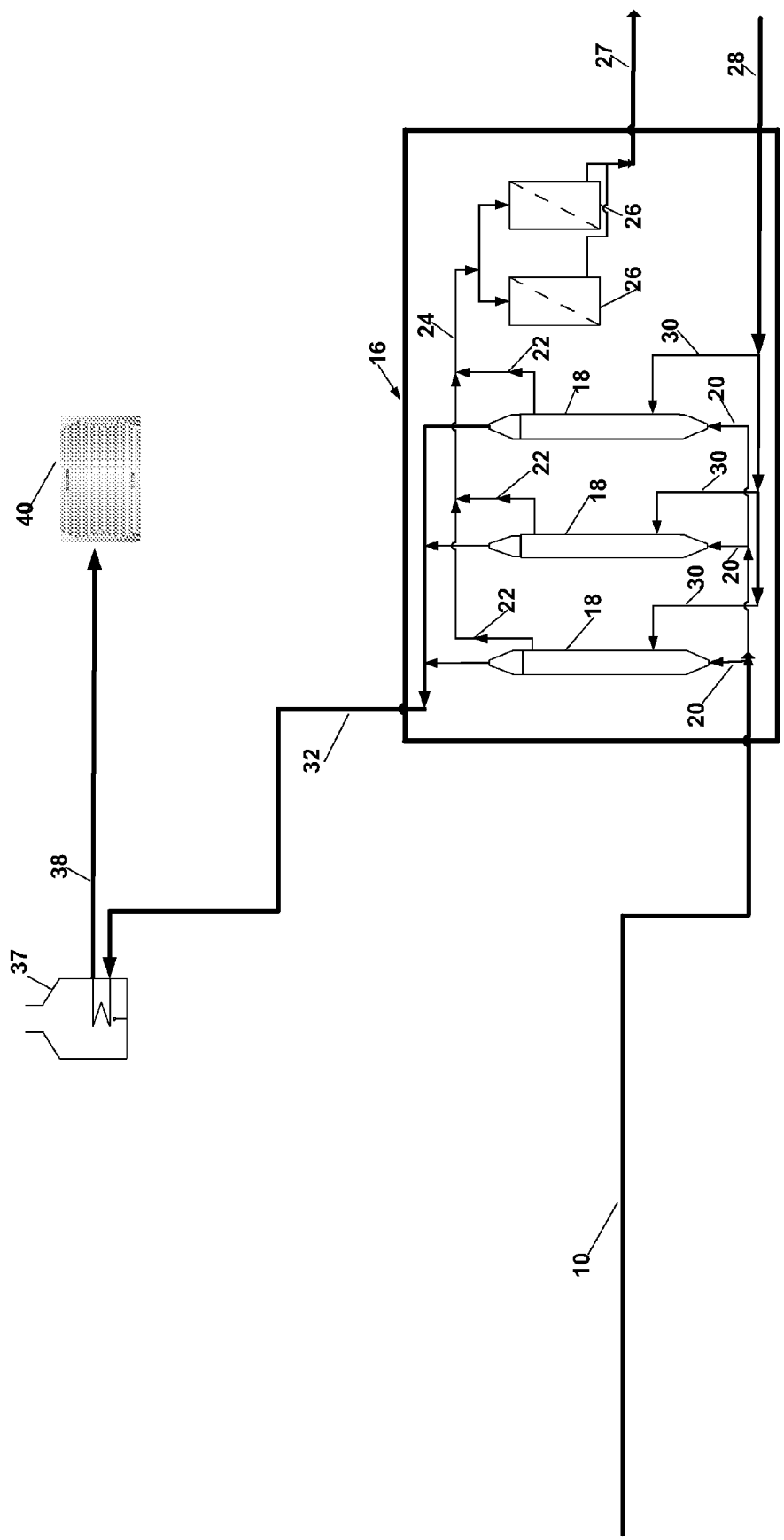
FIG. 2 is a schematic drawing of a process arrangement for biologically converting a sulfur containing syngas stream into liquid products in accordance with this invention.

FIG. 2 gives a general overview of a process arrangement and shows major components of the process for biologically converting a sulfur containing syngas stream into liquid products in simplified form. While the major syngas components are consumed in the bioreactor to produce liquid fuel components, H2S or other sulfur compounds are consumed in the bioreactor to maintain microorganism metabolic activity. A stream of clean syngas enters the process via a line 10 and enters a bioreactor section 16. Line 10 feeds the syngas stream to a trio of bioreactors 18 via distribution lines 20. The syngas contacts the fermentation liquid in the bioreactors 18 and the microorganisms consume the CO, and CO2 and H2 and convert it into liquid products therein. A series of collection lines 22 withdraw fermentation liquid containing liquid products and cellular material from the microorganisms contained in each bioreactor 18. A line 24 transfers the fermentation liquid via to purification zones 26. Before the fermentation liquid passes to a separation zone for the recovery of liquid products, in one instance ethanol, the purification zone 26 removes biological materials and other dissolved matter. The purification zone may use any suitable means such as filtration or ultra-filtration to recover these materials. Microorganisms retained in the purification zone may be returned to the fermentor. After purification, the rest of the fermentation liquid passes to a liquid product separation zone via a line 27, such as for the recovery of ethanol. Fermentation liquid recovered from the liquid product separation zone returns to the bioreactors 18 via return line 28 and distribution lines 30.

A collection line 32 recovers the tail gas from bioreactors 18 and delivers it to a Thermal Oxidizer/Steam generation equipment system 37. Hot exhaust gas or steam from Thermal Oxidizer goes via line 38 to supply plant energy requirements for plant equipment 40. Most gaseous sulfur compounds in the tail gas, such as H2S are sent to the Thermal Oxidizer/Steam generation system 37, where the sulfur compounds are converted to SOX. Conventional SOX removal techniques such as wet lime processes can be employed as required by applicable environmental regulations. This invention may be applied to any bioconversion process that produces an aqueous stream containing a dilute concentration of ethanol.

Bioconversions of CO and H2/CO2 to acetic acid, n-butanol, butyric acid, ethanol, propanol, propionic acid, and other products are well known. In a recent book, concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of *Biochemistry and Physiology of Anaerobic Bacteria*, L. G. Ljungdahl eds. Spring er (2003). Any suitable microorganisms that have the ability to convert the syngas components: CO, H2, CO2 individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; and, U.S. patent Ser. No. 12/891,515 filed Sep. 27, 2010 entitled A Novel Propanologenic *Clostridium* Species, *Clostridium neopropanologen* having all of the identifying characteristics of ATCC No. PTA-11281, all of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol. *Clostridium neopropanologen* may be used, for example, to ferment syngas to propanol and propionic acid.

Suitable microorganisms and growth conditions include the anaerobic bacteria *Butyribacterium methylotrophicum*, having the identifying characteristics of ATCC 33266, which can be adapted to CO and used; this will enable the production of n-butanol as well as butyric acid as taught in the references: "*Evidence for Production of n-Butanol from Carbon Monoxide by Butyribacterium methylotrophicum*," Journal of Fermentation and Bioengineering, vol. 72, 1991, p. 58-60; "*Production of butanol and ethanol from synthesis gas via fermentation*," FUEL, vol. 70, May 1991, p. 615-619. Other suitable microorganisms include *Clostridium Ljungdahli*, with strains having the identifying characteristics of ATCC 49587 (U.S. Pat. No. 5,173,429) and ATCC 55988 and 55989 (US-A-6,136,577) that will enable the production of ethanol as well as acetic acid and *Clostridium autoethanogenum* sp. nov., an anaerobic bacterium that produces ethanol from carbon monoxide. Jamal Abrini, Henry Naveau, Edmond-Jacques Nyns, *Arch Microbiol.*, 1994, 345-351; Archives of Microbiology 1994, 161: 345-351. All of these references are incorporated herein in their entirety.

The biological conversion of syngas to alcohols, including but not necessarily limited to ethanol, propanol, propionic acid, butanol, and so forth, is a process that requires microorganisms that must maintain metabolic activity by biological processes that consume certain types of amino acids. Amino acids useful to microorganisms to maintain biological activity include sulfur containing amino acids, such as methionine, cysteine, and/or cystine. In bioreactor systems for the production of alcohols such as ethanol from syngas, sulfur containing amino acids can be supplied to meet microorganism sulfur demand needed to maintain metabolic activity. Alternately, sulfur compounds, such as H2S, can be provided to the microorganisms, which in turn convert these sulfur compounds to the required sulfur containing compounds needed to maintain metabolic activity. Thus, as the microorganisms consume sulfur containing amino acids, the consumed amino acids can be replaced either directly or produced by the microorganism from sulfur compounds, such as H2S, that are in the bioreactor feed syngas.

The microorganisms found suitable thus far for this invention require anaerobic growth conditions. Therefore, the system will employ suitable control and sealing methods to limit the introduction of oxygen into the system. Since the organisms reside principally in contact with the liquid volume of the retention chamber the system maintains a suitable redox potential in the liquid and this chamber may be monitored to insure anaerobic conditions. Anaerobic conditions in the retained liquid volume are usually defined as having a redox potential of less than −200 mV and preferably a redox potential in the range of from −300 to −560 mV. To further minimize exposure of the microorganisms to oxygen, the feed gas will preferably have an oxygen concentration of less than 1000 ppm, more preferably less than 100 ppm, and even more preferably less than 10 ppm.

The instant invention can use any type of bioreactor to retain the microorganisms for the conversion of the syngas. Many devices and equipment are used for gas transfer to microorganisms in fermentation and waste treatment applications. Conventional systems will retain a substantial volume of fermentation liquid in a vessel or column and use means for agitation to promote mass transfer between the relatively insoluble syngas components and the microorganisms retained in the fermentation liquid. In application of this invention to the production of liquid products from gas streams, in particular CO or a mixture of CO2 and H2, the liquid column will typically comprise a bioreactor that retains microorganisms suspended in a fermentation liquid. Specific types of bioreactors include bubble column bioreactors and stirred tank bioreactors. These conventional bioreactors and systems may use agitators with specialized blades or configurations to create a continuous stirred reactor. Other systems use gas lift or fluidized beds, where liquids or gases are circulated via contacting devices. The fluidized systems are generally configured for use with microorganisms in planktonic form, i.e., they exist as individual cells in liquid medium. Gas dissolution rates for such systems are also generally low.

Cell retention by formation of biofilms is a very good and often inexpensive way to increase the density of micro-organisms in bioreactors. This requires a solid matrix with a large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. They suffer from either being very large or unable to provide sufficient gas dissolution rates.

The use of bioreactors that retain biofilms has been proposed for the production of liquid fuels. U.S. Patent Applications 2008/0305539 and 2009/029434 show the use of a bioreactor to support microorganisms on or in a membrane (preferably hollow fiber membranes) for the production of ethanol from syngas. U.S. Patent Application 2009/0035848 shows the use of bioreactor for producing ethanol from syngas using microorganisms retained on media that circulates as a moving bed in a fermentation liquid. In both of these bioreactors, the fermentation liquid retains the desired liquid product such as ethanol from the microorganisms in dilute concentration.

All these systems for conversion of biomass derived syngas rely on a fermentation broth that provides a low concentration of ethanol in a relatively large volume of aqueous liquid. Ethanol concentration will ordinarily fall below 6% and in most cases less than 4%. As a result, practical recovery of ethanol from the fermentation broth requires a separation system that can efficiently recover the ethanol from the dilute fermentation liquid.

Depending on the nature of the liquid product produced, there are a number of technologies that can be used for product recovery. Methods for recovering ethanol from fermentation liquids are well known and include traditional distillation methods. For example, distillation, dephlegmation, pervaporation, and liquid-liquid extraction can be used for the recovery of ethanol, propanol, propionic acid, and n-butanol, whereas electrodialysis and ion-exchange can be used for the recovery of acetate, butyrate, and other ionic products. U.S. Pat. Nos. 6,899,743 B2 and 6,755,975 B2 disclose processes for recovering organic compounds such as ethanol from water by the use of pervaporation followed by dephlegmation.

In addition to low concentrations of the desired liquid product, such as ethanol, the fermentation liquid, as with any biological process, will contain other dissolved and undissolved components. Such components include cells, proteins, salts, unfermented solubles, and colloidal materials. These materials can impose impurities into the separation processes thereby requiring additional separation steps and purification steps for the recovery of ethanol or other liquid products.

This separation and removal of the CO2 after the bioreactor is a useful step in this process invention and the compatibility of these temperatures promotes integration with the typical process operating conditions, which are moderate pressures (3 to 7 atmospheres) and temperatures (35 to 50 C).

Separation of CO2 from CO and H2 can be done by several technologies such as absorption desorption, scrubbing/extraction by amines, or membranes. U.S. Pat. Nos. 5,558,698, 4,597,777, and the references described therein disclose a number of membranes and methods for effecting such separations. The membrane-based technologies may be particularly suitable because of their modularity and operability at the temperatures and pressures provided. Since the CO2 separation is not required at high levels and separation of approximately 70% or greater is acceptable, membrane systems are ideal process systems to meet these requirements. There are several companies that can provide membrane systems to meet these requirements (Air Liquide, Air Products, Guild Associates, etc.) In addition, recent advances in certain zeolite adsorbents where the pore size has been reduced from 4 A to 3.7 A has led to the "Molecular Gate" technology, where CO2 and other smaller gas molecules are adsorbed and readily separated. This technology, originally developed by Englehard Corporation, is licensed by Guild Associates (Dublin, Ohio). More information on this technology can be found at: www.moleculargate.com.

Classic amine and methanol based extraction technologies are also suitable and several operate at moderate pressures and near ambient conditions. The CO2 that will be desorbed from the regeneration of the amine extract will be essentially free of combustible gasses and can be vented or used for CO2 applications.

The CO2 may also find application within the plant itself. Since the preferred gasification systems for this invention will normally operate under oxygen starved conditions, an inert purge medium routinely enters the feed system to displace air that could enter with the feed. The recovered CO2 can provide a ready source for the purge medium.

Figure 3:
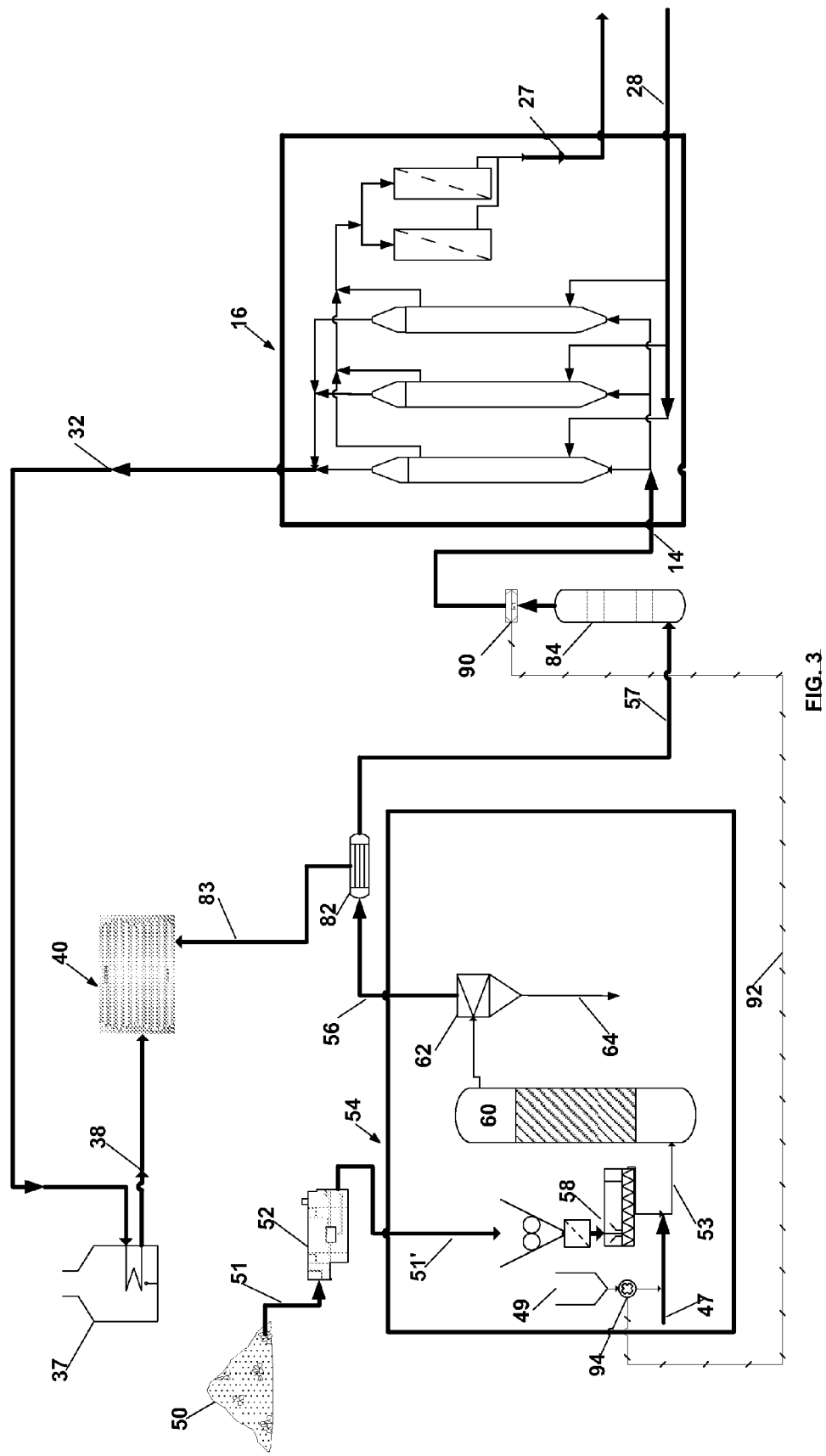
FIG. 3 is a schematic drawing of a process arrangement showing the generation of a sulfur containing syngas from biomass and the biological conversion of the sulfur containing syngas stream into liquid products in accordance with this invention.

FIG. 3 provides a more complete description of the process arrangement showing the generation of syngas from biomass and the biological conversion of a sulfur containing syngas stream into liquid products within the context of a descriptive flow diagram. FIG. 3 shows woody biomass 50 as the starting material. Transfer lines 51 and 51' convey the woody biomass to the solids transport system 58. The woody biomass has about 20% moisture content prior to entering the gasification process section 54. If necessary, the woody biomass may pass through an optional drier 52 to adjust its moisture content. The woody biomass is optionally mixed with a heat transfer bed material, such as coke or coal, and the mixture is conveyed via transfer line 53 to the gasifier 60. A sulfur control additive can be added to the woody biomass via hopper 49 and conveyed to the gasification process via transfer lines 47 and 53. Optionally, a residue melting point modifier can also be charged to the process via transfer line 47 or through a separate transfer line.

The gasification section converts the woody biomass into the primary syngas stream carried by a line 56. Within the gasification section, a solids transport system 58 conveys the woody biomass via transfer lines 53 and 47 at a continuous controlled rate to the gasification reaction chamber 60, where hot gasification reaction products intensely contacts the biomass to produce a syngas and residue. Particulates, along with the syngas, flow out of the top of chamber 60 and optionally into a solids separation system 62 that separates the syngas stream from the particulates. The particulates flow from separation system 62 via a line 64 and are collected for further utilization or disposal.

The syngas is taken overhead from separation system 62 via a line 56. The syngas undergoes further conditioning before entering the bioreactor section 16. The syngas, typically at a temperature of 1000 to 1200° C. and at pressures of 7 bars, is cooled to about 40° C. by a series of heat exchangers 82 and the steam is recovered for power and energy production. Heat exchangers 82 produce additional steam to a supply of steam taken via line 83 for plant equipment 40. At least a portion of the cooled gas 57 is further scrubbed with aqueous fluids and filtered to remove particulates and residual tarry materials in syngas clean-up section 84.

The syngas is now fed in the manner previously described with respect to FIG. 2 to a series of bioreactors via line 14. The concentration of H2S and other measurable sulfur compounds are measured by sensor 90. As known in the art, the measured sulfur concentration is communicated to the sulfur control additive feeder 94 via communication link 92. The feeder 94 controls the rate of addition of the sulfur control additive to the gasification reactor chamber 60. The feeder 94 rate can be adjusted automatically so as to maintain a desired sulfur concentration in the syngas feed to bioreactor section 16. In some embodiments of the invention, the sulfur concentration in the syngas can be controlled relative to the metabolic demand in the bioreactor section. Accordingly, the desired sulfur concentration in the syngas can vary from a minus one hundred percent to a plus five hundred percent of the metabolic demand for sulfur in the bioreactor section. The bioreactors again contain the microorganisms that convert the CO and H2/CO2 to the desired liquid products. Bioconversion processes can use the CO and H2/CO2 from the feed syngas and convert it to the desired products with a high degree of conversion and selectivity. For example, using strains of the microorganisms such as *C. Ragsdali, C. Ljungdahli*, and/or *C. autoethanogenium*, the CO and H2/CO2 can be converted to ethanol with almost 95% of the theoretical selectivity as shown in the following equations.

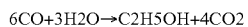

6CO+3H2O→C2H5OH+4CO2

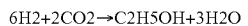

6H2+2CO2→C2H5OH+3H2O

The remaining H2S and other biologically useful sulfur compounds in the syngas are absorbed by the microorganism in the bioreactor and utilized to maintain bacteria metabolic activity. The CO2 has no energy value and has to be removed from the process. The fermentation liquid passes to the liquid product, such as ethanol, separation zone via line 27 and recovered fermentation liquid returns to the bioreactors via line 28.

The tail gas passes via line 32 to the Thermal Oxidizer/Steam generation equipment system 37. Hot exhaust gas or steam from Thermal Oxidizer goes via line 38 to supply plant energy requirements for plant equipment 40. Most gaseous sulfur compounds in the tail gas, such as H2S are sent to the Thermal Oxidizer/Steam generation system 37 where the sulfur compounds are converted to SOX. Conventional SOX removal techniques such as wet lime processes can be employed as required by applicable environmental regulations.

While preferred embodiments and example configurations of the invention have been herein illustrated, shown, and described, it is to be appreciated that various changes, rearrangements and modifications may be made therein, without departing from the scope of the invention as defined by the appended claims. It is intended that the specific embodiments and configurations disclosed are illustrative of the preferred and best modes for practicing the invention, and should not be interpreted as limitations on the scope of the invention as defined by the appended claims; it is to be appreciated that various changes, rearrangements, and modifications may be made therein, without departing from the scope of the invention as defined by the appended claims.

The invention claimed is:

1. A process for producing liquid products from biomass generated syngas using microorganisms having metabolic processes that utilize sulfur in limited amounts, the method comprising:
   a) charging a biomass feed containing sulfur compounds to a gasification unit;
   b) heating the biomass feed in an oxygen controlled atmosphere within the gasification unit to produce a gasifier residue, gaseous sulfur or sulfur compounds, and syngas containing at least one of CO or a mixture of $CO_2$ and $H_2$;
   c) adding a sulfur control additive at an adjustable rate to a heated zone of the gasification unit produced by step b) thereby generating a sulfide compound that becomes part of the gasifier residue and reduces the sulfur or sulfur compounds in the syngas, wherein the rate of sulfur control additive addition is adjusted in response to a measured concentration of sulfur in the sulfur containing syngas;

d) removing the gasifier residue from the gasification unit;

e) collecting gaseous sulfur or sulfur compounds with the syngas from the gasification unit to produce sulfur containing syngas and passing at least a portion of the sulfur containing syngas to a bioreactor;

f) contacting the sulfur containing syngas in the bioreactor with microorganisms to convert at least a portion of the syngas components to the liquid products and to provide sulfur to the microorganisms, wherein the microorganisms in the bioreactor comprises a mono-culture or a co-culture of microorganisms requiring anaerobic growth condition and that require a minimum amount of sulfur for their metabolic function and producing liquid products while not exceeding a maximum amount of sulfur that will reduce the microorganisms production of liquid products; and, g) recovering a fermentation liquid from the bioreactor containing the liquid products.

2. The process of claim 1, wherein the biomass comprises carbonaceous materials selected from one or more the group consisting of wood, miscanthus, switchgrass, sugar cane bagasse, corn stover, urban waste, and recycled bioreactor waste.

3. The process of claim 1, wherein the gasifier residue is rapidly removed from the gasification unit before sulfur and metals in the gasifier residue evolve back into the syngas.

4. The process of claim 1 wherein the heated zone of the gasification unit operates at a temperature of from 500 to 4000.degree.C.

5. The process of claim 3, wherein the residue from the gasification unit comprises one or more of the group consisting of a molten slag, an agglomerated ash, and a particulate.

6. The process of claim 3, further comprising charging a gasifier residue melting point modifier to the gasification unit.

7. The process of claim 1, further comprising charging steam or water to the gasification unit.

8. The process of claim 1, further comprising recovering heat from at least a portion of sulfur containing syngas from the gasification unit before contacting the syngas with microorganisms in the bioreactor and using the recovered heat to generate steam for at least one of drying the biomass feed or recovering products from the fermentation.

9. The process of claim 1, wherein the adjustable rate for adding the sulfur control additive is adjusted to produce a desired concentration of sulfur contributed to the bioreactor from the sulfur containing syngas that ranges from minus 100 to plus 500 percent of a metabolic sulfur demand of the microorganisms.

10. The process of claim 1, further comprising adding the sulfur control additive to the heated zone of the gasification unit at an adjustable rate.

11. The process of claim 1, wherein the sulfur control additive comprises at least one of the group of oxides, salts, and elemental forms of transition metals.

12. The process of claim 1, wherein the sulfur control additive comprises at least one of the group iron, iron oxide, zinc, zinc oxide, manganese, and manganese oxide.

13. The process of claim 1, wherein the liquid products comprise at least one of ethanol, propanol, propionic acid, acetic acid, butanol, or butyric acid.

14. The process of claim 1 wherein the microorganisms in the bioreactor comprises a mono-culture or a co-culture of at least one of *Clostridium ragsdalei, Butyribacterium methylotrophicum, Clostridium ljungdahlii, Clostridium autoetha-* *nogenum, Clostridium woodii, Clostridium neopropanologen* and *Clostridium carboxydivorans*.

15. The process of claim 1, further comprising charging an oxygen containing gaseous feed to the gasification unit wherein the oxygen containing gaseous feed is selected form one or more of the group of air, oxygen enriched air, and essentially pure oxygen.

16. The process of claim 14 wherein the fermentation liquid comprises ethanol in a concentration of at least 0.1 wt %.

17. A process for producing liquid products from biomass generated syngas using microorganisms having metabolic processes that utilize sulfur in limited amounts, the method comprising:

a) charging a biomass feed containing sulfur compounds to a gasification unit;

b) heating the biomass feed in an oxygen controlled atmosphere within the gasification unit to produce a molten gasifier residue, gaseous sulfur or sulfur compounds, and syngas containing at least one of CO or a mixture of $CO_2$ and $H_2$;

c) adding a sulfur control additive comprising at least one of oxides, salts or elemental forms of transition metals to a heated zone of the gasification unit at an adjustable rate to generate a sulfide compound that melts at the temperature of the gasification and becomes part of the molten gasifier residue to produce a gasifier residue containing sulfur and to lower the concentration of the sulfur or sulfur compounds in the syngas;

d) removing the molten gasifier residue containing sulfur from the gasification unit,wherein the gasifier residue is rapidly removed from the gasification unit before sulfur and metals in the gasifier residue evolve back into the syngas;

e) collecting gaseous sulfur or sulfur compounds with the syngas from the gasification unit to produce sulfur containing syngas and passing at least a portion of the sulfur containing syngas to a bioreactor;

f) contacting the sulfur containing syngas in the bioreactor with microorganisms to convert at least a portion of the syngas components to the liquid products and to provide sulfur to the microorganisms,wherein the microorganisms in the bioreactor comprises a mono-culture or a co-culture of microorganisms requiring anaerobic growth condition and that require a minimum amount of sulfur for their metabolic function and producing liquid products while not exceeding a maximum amount of sulfur that will reduce the microorganisms production of liquid products;

g) measuring a concentration of sulfur in the sulfur containing syngas and adjusting the rate of sulfur control additive addition to the gasification unit in response to a measured concentration of sulfur in the sulfur containing syngas; and, h) recovering a fermentation liquid from the bioreactor containing the liquid products.

18. The process of claim 17, wherein the heated zone of the gasifier operates at a temperature of from 500 to 4000.degree. C.

19. The process of claim 17, further comprising charging a gasifier residue melting point modifier to the gasification unit.

20. The process of claim 17, wherein the adjustable rate for adding the sulfur control additive is adjusted to produce a desired concentration of sulfur in the sulfur containing syngas that ranges from minus 100 to plus 500 percent of a metabolic sulfur demand of the microorganisms.

21. The process of claim 17, wherein the liquid products comprise at least one of ethanol, propanol, acetic acid, propionic acid, butanol, or butyric acid.

22. The process of claim 17, wherein the microorganisms in the bioreactor comprises a mono-culture or a co-culture of at least one of *Clostridium ragsdalei, Butyribacterium methylotrophicum, Clostridium ljungdahlii, Clostridium autoethanogenum, Clostridium woodii, Clostridium neopropanologen* and *Clostridium carboxydivorans*.

23. The process of claim 17, wherein the fermentation liquid comprises ethanol in a concentration of an at least 0.1 wt %.

24. A process for producing ethanol from biomass generated syngas using microorganisms having metabolic processes that utilize sulfur in limited amounts, the method comprising:
   a) charging a biomass feed containing sulfur compounds to a gasification unit;
   b) charging an oxygen containing gaseous feed to the gasification unit and heating the biomass feed in an oxygen controlled atmosphere within the gasification unit to produce a molten slag, gaseous sulfur or sulfur compounds, and syngas containing at least one of CO or a mixture of $CO_2$ and $H_2$;
   c) adding a sulfur control additive comprising at least one of oxides, salts or elemental forms of transition metals at an adjustable rate to a zone of the gasification unit that generates a sulfide compound that melts at the temperature of the gasification and becomes part of the molten slag to produce a slag containing sulfur and to reduce the sulfur or sulfur compounds in the syngas;
   d) removing the molten slag containing sulfur from the gasification unit, wherein the molten slag is rapidly removed from the gasification unit before sulfur and metals in the molten slag evolve back into the syngas;
   e) collecting gaseous sulfur or sulfur compounds with the syngas from the gasification unit to produce sulfur containing syngas in a concentration that ranges from minus 100 to plus 500 of the metabolic demand of the microorganisms and passing at least a portion of the sulfur containing syngas to a bioreactor;
   f) contacting the sulfur containing syngas in the bioreactor with microorganisms to convert at least a portion of the syngas components to the liquid products and to supply sulfur compounds to the microorganisms, wherein the microorganisms in the bioreactor comprises a mono-culture or a co-culture of microorganisms requiring anaerobic growth condition and that require a minimum amount of sulfur for their metabolic function and producing liquid products while not exceeding a maximum amount of sulfur that will reduce the microorganisms production of liquid products;
   g) measuring the concentration of sulfur in the sulfur containing syngas and adjusting the rate of sulfur control additive addition to the gasification unit in response to the measured concentration of sulfur in the sulfur containing syngas;
   h) recovering a fermentation liquid from the bioreactor containing ethanol in a concentration of at least 0.1 wt %; and,
   i) recovering heat from at least a portion of the sulfur containing syngas upstream of the bioreactor and using the recovered heat to generate steam for at least one of drying the biomass feed or recovering products from the fermentation.

25. The process of claim 24, wherein the microorganisms in the bioreactor comprises a mono-culture or a co-culture of at least one of *Clostridium ragsdalei, Butyribacterium methylotrophicum, Clostridium ljungdahlii, Clostridium autoethanogenum, Clostridium woodii, Clostridium neopropanologen* and *Clostridium carboxydivorans*.

* * * * *